(12) United States Patent
Jia et al.

(10) Patent No.: US 11,200,665 B2
(45) Date of Patent: Dec. 14, 2021

(54) FUNDUS IMAGE PROCESSING METHOD, COMPUTER APPARATUS, AND STORAGE MEDIUM

(71) Applicants: SHANGHAI SIXTH PEOPLE'S HOSPITAL, Shanghai (CN); SHANGHAI JIAO TONG UNIVERSITY, Shanghai (CN)

(72) Inventors: Weiping Jia, Shanghai (CN); Bin Sheng, Shanghai (CN); Huating Li, Shanghai (CN); Ling Dai, Shanghai (CN)

(73) Assignees: SHANGHAI SIXTH PEOPLE'S HOSPITAL, Shanghai (CN); SHANGHAI JIAO TONG UNIVERSITY, Shanghai (CN)

( * ) Notice: Subject to any disclaimer, the term of this patent is extended or adjusted under 35 U.S.C. 154(b) by 525 days.

(21) Appl. No.: 16/302,410

(22) PCT Filed: May 14, 2018

(86) PCT No.: PCT/CN2018/086739
§ 371 (c)(1),
(2) Date: Nov. 16, 2018

(87) PCT Pub. No.: WO2019/024568
PCT Pub. Date: Feb. 7, 2019

(65) Prior Publication Data
US 2021/0224977 A1 Jul. 22, 2021

(30) Foreign Application Priority Data

Aug. 2, 2017 (CN) .......................... 201710653516.X
Apr. 16, 2018 (CN) .......................... 201810340025.4

(51) Int. Cl.
*G06K 9/00* (2006.01)
*G06T 7/00* (2017.01)
(Continued)

(52) U.S. Cl.
CPC .............. *G06T 7/0012* (2013.01); *A61B 3/12* (2013.01); *G06K 9/629* (2013.01); *G06K 9/6261* (2013.01);
(Continued)

(58) Field of Classification Search
CPC ......... G06T 7/0012; G06T 2207/30096; G06T 2207/20132; G06T 2207/30041;
(Continued)

(56) References Cited

U.S. PATENT DOCUMENTS

2002/0052551 A1* 5/2002 Sinclair ................ A61B 3/0025
600/476
2014/0276025 A1* 9/2014 Durbin ..................... A61B 3/18
600/427

(Continued)

FOREIGN PATENT DOCUMENTS

CN 106874889 A 6/2017
CN 106934798 A 7/2017
(Continued)

OTHER PUBLICATIONS

International Search Report from International Application No. PCT/CN2018/086739 dated Jul. 25, 2018.
(Continued)

*Primary Examiner* — Shervin K Nakhjavan
(74) *Attorney, Agent, or Firm* — Marcus S. Simon

(57) ABSTRACT

A fundus image processing method comprising: receiving a collected fundus image; identifying the fundus image via a first neural network to generate a first feature set of the fundus image; identifying the fundus image via a second
(Continued)

neural network to generate a second feature set of the fundus image, wherein the first feature set and the second feature set indicate different lesion attributes of the fundus image; combining the first feature set and the second feature set to obtain a combined feature set of the fundus image; and inputting the combined feature set into a classifier to obtain a classification result.

17 Claims, 4 Drawing Sheets

(51) Int. Cl.
    *G16H 30/20*         (2018.01)
    *G16H 50/70*         (2018.01)
    *G16H 50/20*         (2018.01)
    *G16H 30/40*         (2018.01)
    *A61B 3/12*          (2006.01)
    *G06K 9/62*          (2006.01)
    *G06N 3/04*          (2006.01)

(52) U.S. Cl.
    CPC ......... *G06K 9/6267* (2013.01); *G06N 3/0454* (2013.01); *G16H 30/20* (2018.01); *G16H 30/40* (2018.01); *G16H 50/20* (2018.01); *G16H 50/70* (2018.01); *G06K 2209/05* (2013.01); *G06T 2207/20084* (2013.01); *G06T 2207/20132* (2013.01); *G06T 2207/30041* (2013.01); *G06T 2207/30096* (2013.01)

(58) Field of Classification Search
    CPC .......... G06T 2207/20084; G16H 30/40; G16H 50/20; G16H 30/20; G16H 50/70; A61B 3/12; G06K 9/6261; G06K 9/629; G06K 9/6267; G06K 2209/05; G06N 3/0454
See application file for complete search history.

(56) References Cited

U.S. PATENT DOCUMENTS

| | | | |
|---|---|---|---|
| 2016/0292856 | A1 | 10/2016 | Niemeijer et al. |
| 2018/0315193 | A1* | 11/2018 | Paschalakis ............. G06N 3/08 |
| 2019/0206054 | A1* | 7/2019 | Mao .......................... A61B 3/12 |
| 2020/0160521 | A1* | 5/2020 | Wang .................... A61B 3/0025 |
| 2020/0202527 | A1* | 6/2020 | Choi ...................... A61B 5/021 |
| 2020/0211235 | A1* | 7/2020 | Hsu ........................ G06K 9/4628 |
| 2020/0250497 | A1* | 8/2020 | Peng ..................... G06K 9/6277 |
| 2020/0250821 | A1* | 8/2020 | Peng ..................... G06K 9/6256 |
| 2020/0323480 | A1* | 10/2020 | Shaked ..................... G01N 1/30 |
| 2021/0082566 | A1* | 3/2021 | Do ............................ G06N 3/08 |
| 2021/0104313 | A1* | 4/2021 | Mizobe .................. G16H 30/40 |

FOREIGN PATENT DOCUMENTS

| | | |
|---|---|---|
| CN | 107045720 A | 8/2017 |
| CN | 107358605 A | 11/2017 |
| CN | 107358606 A | 11/2017 |
| CN | 107423571 A | 12/2017 |

OTHER PUBLICATIONS

Ding, Pengli et al., "Diabetic retinal image classification method based on deep neural network", Journal of Computer Applications ISSN 1001-9081, Mar. 10, 2017, 6 pages.

* cited by examiner

FUNDUS IMAGE PROCESSING METHOD, COMPUTER APPARATUS, AND STORAGE MEDIUM

CROSS-REFERENCE TO RELATED APPLICATIONS

This application claims priority to PCT International Application No. PCT/CN2018/086739 filed on May 14, 2018, which claims priority to Chinese Patent Application No. 201710653516X, entitled "LESION IMAGE PROCESSING METHOD, DEVICE, COMPUTER APPARATUS, AND STORAGE MEDIUM" filed Aug. 2, 2017, and Chinese Patent Application No. 2018103400254, entitled "FUNDUS IMAGE PROCESSING METHOD, DEVICE, COMPUTER APPARATUS, AND STORAGE MEDIUM" filed Apr. 16, 2018, the contents of each of the foregoing applications are expressly incorporated herein by reference in its entirety.

TECHNICAL FIELD

The present disclosure relates to a fundus image processing method, a computer apparatus, and a storage medium.

BACKGROUND

In recent years, artificial intelligence has achieved remarkable development in various fields. An important branch of artificial intelligence is to simulate the human brain through machine learning for analytical learning to achieve the purpose of interpreting data such as images, sounds, and text.

Currently, in terms of identification of fundus images, a main identification method still relies on the naked eye to diagnose whether a patient has fundus diseases and a severity of fundus diseases based on the experience of doctors. This artificial identification method is time-consuming and labor-intensive, and is of a low efficiency. The identification of fundus diseases through machine learning is limited to the construction of a single machine learning model, which is of a low identification accuracy.

SUMMARY

According to various embodiments disclosed herein, a fundus image processing method, a computer apparatus, and a storage medium are provided.

A method of processing fundus image includes:
receiving a collected fundus image;
identifying the fundus image via a first neural network to generate a first feature set of the fundus image;
identifying the fundus image via a second neural network to generate a second feature set of the fundus image, wherein the first feature set and the second feature set indicate different lesion attributes of the fundus image;
combining the first feature set and the second feature set to obtain a combined feature set of the fundus image; and
inputting the combined feature set into a classifier to obtain a classification result.

A computer apparatus includes one or more processors and a memory storing computer-readable instructions, which, when executed by the one or more processors, causes the one or more processors to implement steps of the method of processing fundus image provided in any of the embodiments of the present disclosure.

At least one non-transitory computer-readable storage medium stores computer-readable instructions, which, when executed by one or more processors, cause the one or more processors to implement steps of the method of processing fundus image provided in any of the embodiments of the present disclosure.

Details of one or more embodiments of the present disclosure are set forth in the accompanying drawings and description below. Other features and advantages of the present disclosure will become apparent upon review of the description, drawings and claims.

BRIEF DESCRIPTION OF THE DRAWINGS

To illustrate the technical solutions according to the embodiments of the present invention more clearly, the accompanying drawings for describing the embodiments are introduced briefly in the following. Apparently, the accompanying drawings in the following description are only some embodiments of the present invention, and persons of ordinary skill in the art can derive other drawings from the accompanying drawings without creative efforts.

DETAILED DESCRIPTION OF THE EMBODIMENTS

In order to make the objects, technical solutions and advantages of the present application more clear, the present application will be further described in detail below with reference to the accompanying drawings and embodiments. It should be understood that the specific embodiments described herein are merely illustrative and are not intended to be limiting the present application.

Figure 1:
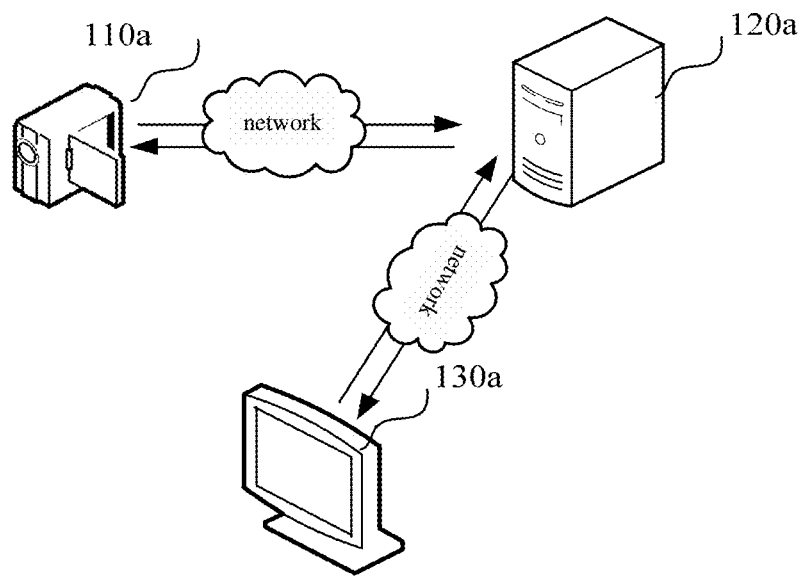
FIG. 1 is a schematic diagram illustrating an environment adapted for a method of processing fundus image in accordance with one or more embodiments.

The method of processing fundus image provided in the present disclosure can be applied to an application environment as shown in FIG. 1. The application environment includes an image collecting device 110a, a server 120a, and a terminal 130a, and the image collecting device 110a and the terminal 130a can communicate with the server 120a via a network. The server 120a can be an individual server or a server cluster composed of a plurality of servers. The terminal 130a can be, but not limited to, various personal computers, notebook computers, smart phones, tablets, and portable wearable devices. The image collecting device 110a can collect a fundus image. The server 120a stores a pre-trained first neural network, a pre-trained second neural network, and a classifier. The server identifies the fundus image via the neural network to obtain a lesion classification result included by the fundus image. The terminal 130*a* receives and displays the classification result generated by the server 120*a*.

Figure 2:
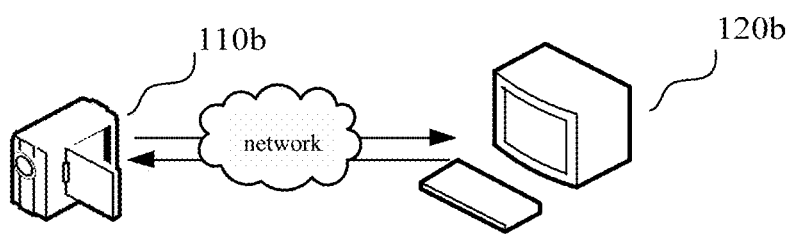
FIG. 2 is a schematic diagram illustrating an environment adapted for a method of processing fundus image in accordance with another embodiment.

In another embodiment, the method of processing fundus image provided by the present disclosure can also apply to an application environment as shown in FIG. 2. The application environment includes an image collecting device 110*b* and a terminal 120*b*, and the image collecting device 110*b* can communicate with the terminal 102*b* via a network. The image collecting device 110*b* can collect a fundus image. The terminal 120*b* stores a pre-trained first neural network, a pre-trained second neural network, and the classifier. The server identifies the fundus image via the neural network, and obtains and displays the lesion classification result included by the fundus image.

Figure 3:
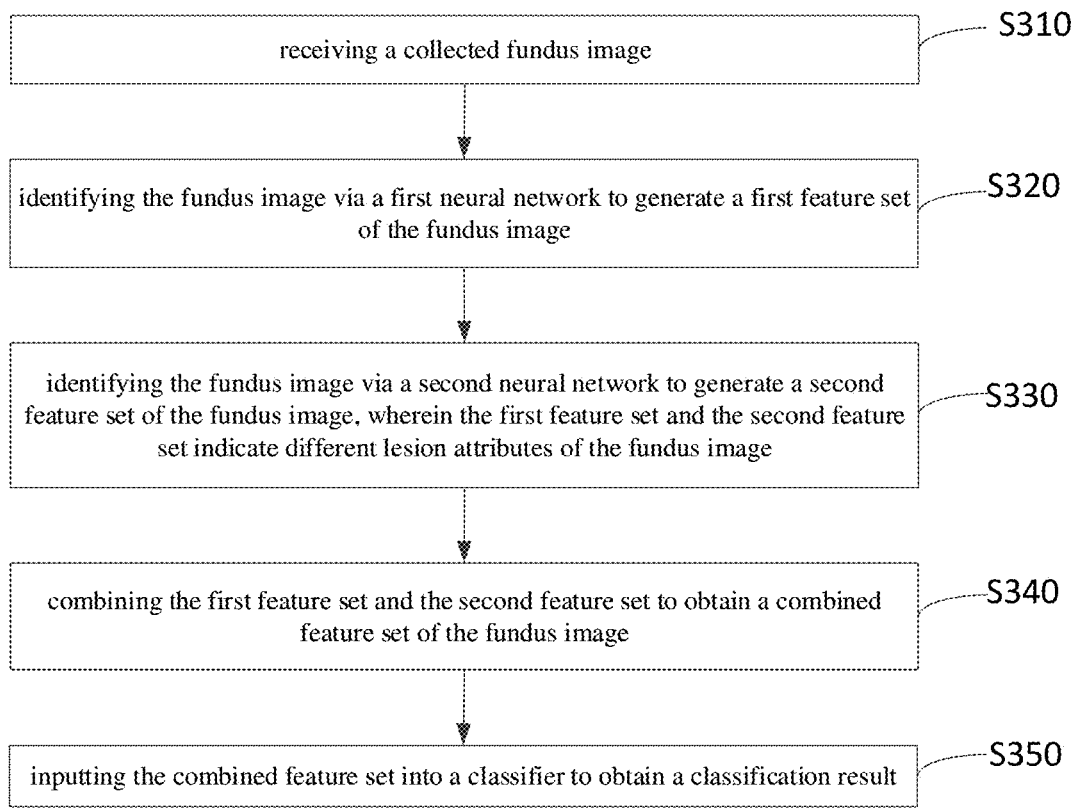
FIG. 3 is a flow chart of a method of processing fundus image in accordance with one or more embodiments.

As shown in FIG. 3, the present disclosure provides a method of processing fundus image, which includes the following steps.

In step S310, a collected fundus image is received.

Figure 4:
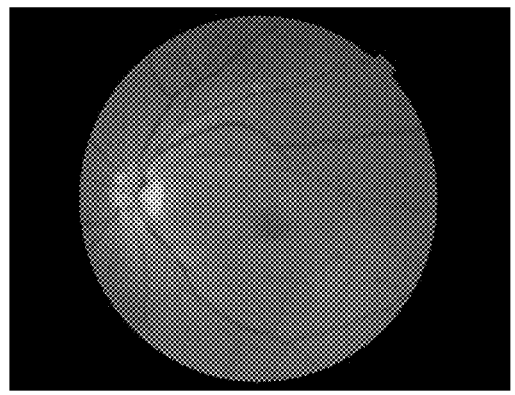
FIG. 4 is a schematic diagram of a collected fundus image.

The collection of the fundus image can be performed via a handheld/fixed medical imaging device. The collected fundus image is shown in FIG. 4. The fundus image collected by the medical imaging device includes an effective fundus image in a middle circular area and a surrounding white or black area, and the surrounding white or black area is a shield portion of a camera, which has no diagnostic significance. Before a model prediction, the fundus image can be pre-processed, such as cutting off pixels without diagnostic significance.

In step S320, the fundus image is identified via the first neural network to generate a first feature set of the fundus image.

In step S330, the fundus image is identified via the second neural network to generate a second feature set of the fundus image, wherein the first feature set and the second feature set indicate different lesion attributes of the fundus image.

Both the aforementioned first and second neural networks are constructed by training historical fundus images. The process of training the neural network is actually a process of learning a preset certain fundus lesion attribute of the training sample.

In this embodiment, the first neural network is trained to be capable of identifying the preset lesion attribute of the fundus image. The collected fundus image is input into the first neural network for identification, and the preset lesion attribute of the fundus image identified by the first neural network is represented by the first feature set. Similarly, the lesion attribute of the fundus image identified by the second neural network is represented by the second feature set.

In this embodiment, it should be understood that both the first feature set and the second feature set are used to describe the lesion attributes of the collected fundus image, but the lesion attributes of the fundus image identified by the first neural network and the second neural network are different, and both complement each other.

The aforementioned feature set can be "feature vector" or "feature sequence", whose meaning should be interpreted in the broadest way.

In step S340, the first feature set and the second feature set are combined to obtain a combined feature set of the fundus image.

The first feature set generated by the first neural network and the second feature set generated by the second neural network are fused to generate the combined feature set. The "combined feature set" herein can be "feature sequence", "feature vector", or the like. In one of the embodiments, the combination of the first feature set and the second feature set is a vector summation of the features.

In step S350, the combined feature set is input into the classifier to obtain a classification result.

The classifier serves as a classifier that ultimately determines the classification result of the fundus image.

In this embodiment, by training two different neural networks (the first neural network and the second neural network), the two neural networks can abstract out features indicating different lesion attributes from the fundus image, that is, extract the lesion features from the fundus image from different angles. The fundus image features at this stage is able to essentially reflect a lesion classification of the fundus image. On this basis, the features of the abstracted different lesion attributes are combined to obtain the combined feature set of the fundus image, and the combined feature set containing more features is input into the classifier as the feature value of the fundus image to be classified and identified again. The classification result obtained by this combination of multiple lesion features and multiple neural network identification is more accurate.

In one embodiment, the classifier in step S350 can be a class II classification model. That is, the fundus image is classified into two levels, such as with lesions and without lesions, or mild lesions and severe lesions. Specifically, the class II classification model can linearly divide the samples into two categories. To take SVM as an example, the basic model thereof is defined as a linear classifier with a large interval on the feature space, then the learning strategy is that the interval is larger, and finally it can be converted into a solution for a convex quadratic programming problem. The purpose of the SVM is to find a hyperplane to divide the sample into two categories with the largest interval. And the w calculated herein represents the coefficient of the hyperplane to be obtained. That is, $$\max \frac{1}{\|w\|}, \text{ s.t., } y_i(w^T x_i + b) \geq 1, i = 1, \ldots, n$$

When no such hyperplane, which can correctly divide the two types of samples divide, exists in the original sample space, the sample can be mapped from the original space to a higher dimensional trait space, so that the sample can be linearly divided into two categories in this new high dimensional space, that is, the sample can be linearly divided in the space. In addition, the choice of a kernel function becomes the maximum variable of a support vector machine (if the kernel function must be used, i.e. nucleation), therefore what kind of kernel function is chosen will affect the final result. The most commonly used kernel functions are: linear kernel, polynomial kernel, Gaussian kernel, Laplacian kernel, sigmoid kernel, and new kernel function obtained by linear combination or direct product and the like between kernel functions.

In another embodiment, the classifier can be a multi-level classification network composed of a plurality of class II classification models in accordance with a preset classification logic. For example, the fundus image is classified into multiple categories. For example, the fundus images are classified into five categories: with no lesions, with mild lesions, with moderate lesions, with severe lesions, PDR and above degree lesions, which are recorded as 0 to 4 grades.

The preset classification logic can be 1-VS-ALL multi-label classification logic, and each sub-class II classification model included in the multi-level classification model can distinguish a certain class of samples specified from other classes. If the classifier is a 5-level classification network, then it contains 5 SVM binary networks, i.e. one SVM is trained for each classification. Class 0 sample is classified for 011234-, class 1 sample is classified for 110234-, class 2 sample is classified for 210134-, class 3 sample is classified for 310124-, and class 4 sample is classified for 410123—respectively.

When training the SVM, the combined feature set obtained after processing by the first neural network and the second neural network is regarded as a feature vector of the fundus image to train the SVM classifier. When training SVM, if the positive and negative samples are not evenly distributed, different weights are given for positive and negative samples. For SVM: 011234, the positive samples are class 0 samples (samples with no lesion), and the negative samples are samples with lesions. If the ratio of the number of current positive samples to the total number of samples is d, then the weight assigned thereto is 1/(2d). The sample weights are set to alleviate the uneven distribution of data, which is equivalent to increasing the number of samples with less data, so that a loss value of these samples is substantially equivalent to that of most samples.

In one embodiment, the first neural network and the second neural network are convolutional neural networks (CNN). The convolutional neural network is a kind of artificial neural network that has a weight sharing network structure. This network structure is more similar to the biological neural network, which reduces the complexity of the network model and reduces the number of the weights. The collected fundus image can be directly used as the input of the network, thus avoiding a complicated feature extraction and data reconstruction process in the conventional recognition algorithm.

Further, the first neural network is a convolutional neural network capable of identifying the lesion type included in the fundus image. The second neural network is a convolutional neural network capable of identifying the lesion level of the fundus lesion contained in the fundus image. In other words, the first feature set indicates a lesion type attribute of the fundus image, and the second feature set indicates a lesion level attribute of the fundus image. The features of two attributes of the lesion type included in the fundus image obtained by predicting by the CNN and the lesion classification of the fundus image are combined, and the combined feature vector includes lesion features of multiple dimensions of the fundus image. The combined feature vector is input into the SVM, and then the obtained fundus lesions classification is more accurate and stable.

Further, the fundus types of the lesion identified by the first neural network can include: microangioma, hard exudation, soft exudation, and hemorrhage. Accordingly, the first feature set output by the first neural network can be a feature vector with a length of 4, and the first neural network is trained such that each element of the output feature vector sequentially represents a corresponding lesion type. For example, if the feature vector output by the first neural network is [1, 0, 0, 0], then it indicates that the fundus image contains microangioma, and does not contain hard exudation, soft exudation, and hemorrhage.

In one embodiment, the lesion level attribute of the fundus image is identified via the second neural network, and a lesion level vector of the fundus image is output. When the fundus lesion is set to include n levels of the lesion, the length of the generated lesion level vector is n−1, and in the feature vector of an i-th level lesion, the i-th element and the elements prior to the i-th element are configured as 1, and the rest elements are configured as 0. For example, the fundus lesion levels that can be identified by the second neural network include: no lesions, mild lesions, moderate lesions, severe lesions, PDR and above degree lesions, recorded as 0 to 4 grades respectively. Accordingly, the second feature set output by the second neural network can be a feature vector with a length of 6. Unlike the One-hot encoding method used in general multi-level classification, the coding method used in the present disclosure is a progressive encoding method. In other words, the training target of the corresponding second neural network is a vector [0, 0, 0, 0] for the class 0, a vector [1, 0, 0, 0,] for the class 1, and a vector [1, 1, 0, 0] for the class 2. That is, for the class i, the i-th element and the elements prior to the i-th element in the target vector are 1 and the rest elements are 0. That is, when the fundus image lesion includes n levels of the lesions, the second feature set generated by the second neural network should be a feature vector with a length of n−1, and in the feature vector of the i-th level lesion, the i-th element and the elements prior to the i-th element are 1, and the rest elements are 0.

The aforementioned fundus lesion classification label coding method of the second neural network conforms to the phenomenon that the lesion is continuously deepened and the new lesion type appears in the presence of the old lesion type.

The training process of the aforementioned first convolutional neural network, the second convolutional neural network, and the classifier will be described as follows.

The training for the first neural network includes that the fundus image is pre-processed in advance to obtain a training sample. The training sample is manually labeled with the lesion types, and the lesion types included in each sample is marked. Each lesion type corresponds to a label, and the target output corresponding to the training sample can be obtained according to the encoding of the label. If the sample image contains microangioma and hard exudation, then the target output of the sample should be [1,1,0,0]. During the training process, the processed image is input into the CNN network for forward propagation, then the difference between the CNN network output and the target output is calculated, and the various parts of the network are derived, and the network parameters are updated via using the SGD algorithm.

The preprocess of the aforementioned fundus image includes:

1. An information area of an image (i.e. an area of interest (AOI)) is acquired. The AOI of the fundus image is the circular area in the middle of a fundus photograph. Only this portion contains the effective fundus image, and the surrounding white or black portion is the occlusion portion of the camera, which has no diagnostic significance.

2. The image is zoomed. The resolution of the fundus photograph is high, usually higher than 1000*2000, which cannot be directly used as the input of the CNN, therefore the image size can be reduced to the required size, which can be 299*299.

3. A single image is normalized. This step is mainly used to avoid the influence of image judgment caused by illumination and the like. This step calculates the average value and standard deviation of the pixel intensity in the AOI for each channel of the image RGB channel. For each pixel, the average value is subtracted from the intensity value and then divided by the standard deviation to obtain the normalized intensity value.

4. A random noise is added. In order to reduce a overfitting problem in the training process and to perform multiple sampling in a prediction process, a Gaussian noise with an average value 0 and a standard deviation which is 5 percent of the image standard deviation is added in the image obtained in the previous step. This will not affect the image discrimination, but also reduce the problem of generalization deficiency caused by over-fitting problems.

5. Random rotation. Since the AOI portion of the image is circular, it is possible to rotate the image at any angle from the center of the picture. Image rotation will not bring any effect on image diagnostics, meanwhile it can reduce the effects of over-fitting problems.

Similarly, before the training of the second neural network and the classifier, the fundus image is also required to be preprocessed as described above. Therefore, the preprocessing process of the image is no longer described in detail when stating the training of the second neural network and the classifier.

The training of the second neural network includes that the fundus image is processed in advance to obtain training samples. The training samples are manually marked, and the lesion level corresponding to each sample is marked, and the target output corresponding to the training samples can be obtained according to the progressive coding method described above. If the fundus image in the sample has 3 levels, then the target output of the sample should be (1, 1, 1, 0). During the training process, the processed image is input into the CNN network for forward propagation, then the difference between the CNN network output and the target output is calculated, then the various portions of the network are derived, and the network parameters are updated via using the SGD algorithm.

Figure 5:
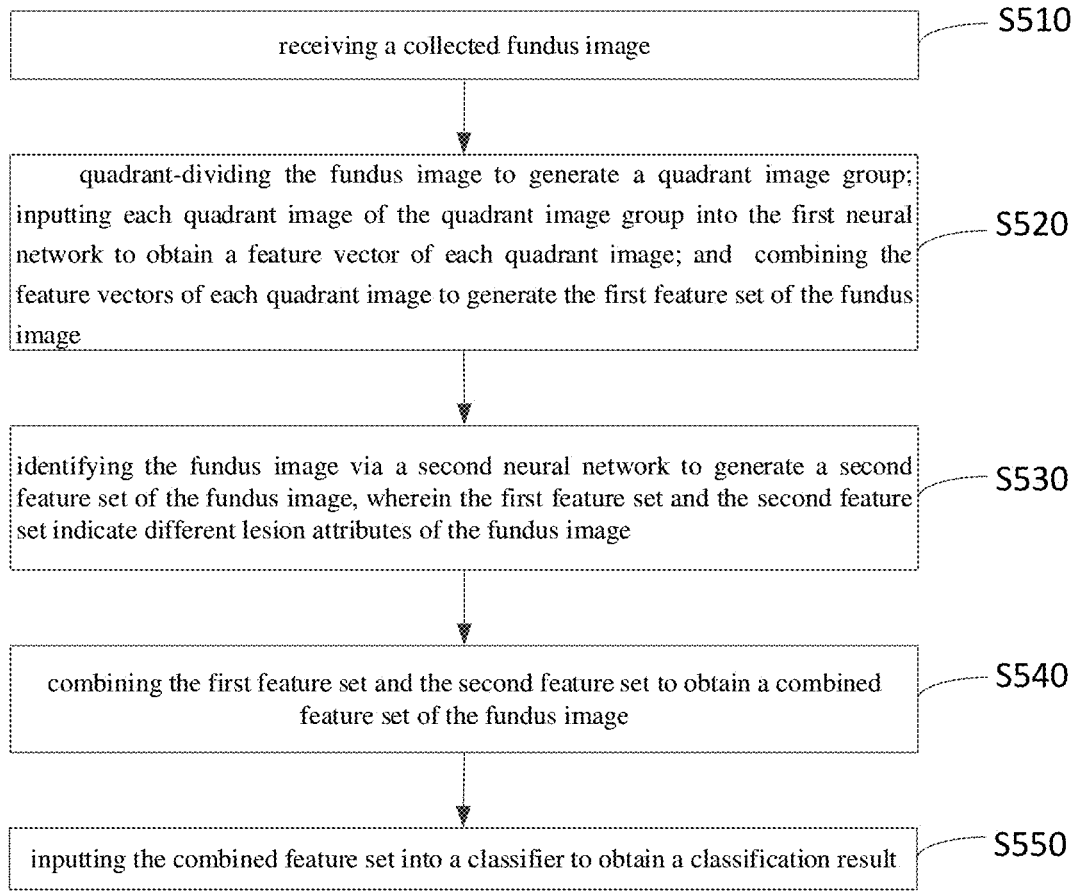
FIG. 5 is a flow chart of a method for processing fundus image in accordance with another embodiment.

In one embodiment, as shown in FIG. 5, a fundus image processing method is provided, which includes the following steps.

In step S510, the collected fundus image is received.

In step S520, the fundus image is quadrant-divided to generate a quadrant image group, each quadrant image in the quadrant image group is input into the first neural network to obtain a feature vector of each quadrant image, and the feature vectors of each quadrant image are combined to generate a first feature set of the fundus image.

Figure 6:
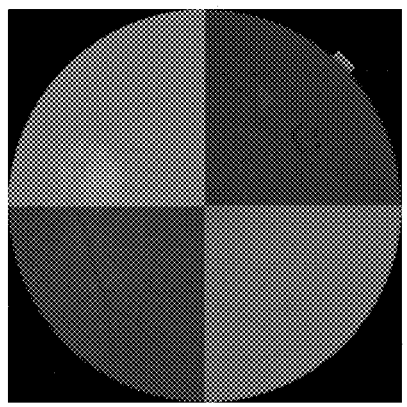
FIG. 6 is a schematic view of quadrant-divided fundus image.
Figure 7:
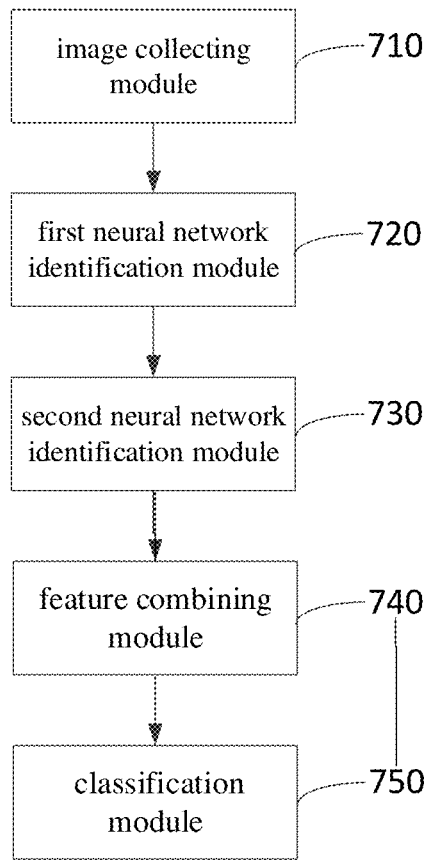
FIG. 7 is a block diagram of a computer apparatus in accordance with one or more embodiments.

As shown in FIG. 6, the quadrant-division divides the fundus image into four regions via using the horizontal and vertical axes in a Cartesian coordinate system. The fundus image in each region is a quadrant image. The quadrant image is zoomed to a preset size, such as 299*299. After processing, the four quadrant images form a quadrant image set.

The quadrant images in the quadrant image set are input to the first neural network for prediction, and each quadrant image produces a feature vector. The first neural network can be a convolutional neural network that identifies an image lesion type, and the feature vector of the output quadrant images of the first neural network can be a vector with a length of 4, and each element in the vector corresponds to a lesion type, such as [1, 0, 0, 0]. The specific definition of the output of the first neural network and the first neural network can be referred to the above definition, and details are not described herein again.

It should be noted that before the quadrant image is input into the first neural network for prediction, the quadrant images are required to be preprocessed in advance. The preprocessing herein can include singularization processing, adding random noise, and random rotation.

The feature vector of the combined quadrant image can be a long feature vector with a length of 16 formed by connecting the feature vectors of the four quadrant images and can be obtained by the feature vector of the first quadrant plus the feature vector of the second quadrant plus the feature vector of the third quadrant and plus the feature vector of the fourth quadrant. The first feature vector generated by the feature vector of the combined quadrant images can not only indicate the lesion types included in the image but also indicate the distribution of different lesion types.

In step S530, the fundus image is identified via the second neural network to generate a second feature set of the fundus image, and the first feature set and the second feature set indicate different lesion attributes of the fundus image.

The specific definition of this step can be referred to the above definition, and details are not described herein again.

In step S540, the first feature set and the second feature set are combined to obtain a combined feature set of the fundus image.

The combined feature set herein includes the first attribute features of the four quadrant images and the second attribute feature of the fundus image.

In step S550, the combined feature set is input into the classifier to obtain a classification result.

The specific definition of this step can be referred to the above definition, and details are not described herein again.

In this embodiment, the combined feature set containing more lesion features is input into the classifier, and the obtained classification result is more accurate.

It should be understood that although the various steps in the flowcharts of FIGS. 3 and 5 are sequentially displayed as indicated by the arrows, these steps are not necessarily performed sequentially in the order indicated by the arrows. Except as explicitly stated herein, the execution of these steps is not strictly limited, and the steps may be performed in other orders. Moreover, at least some of the steps in FIGS. 3 and 5 can include a plurality of sub-steps or stages, which are not necessarily performed at the same time, but can be performed at different times, or the execution order of the sub-steps or stages is not necessarily performed in sequence, but can be performed by turns or alternately with other steps or at least some of the sub-steps or stages of the other steps.

In one embodiment, the collected fundus image can be a fundus image pair, including a left eye image and a right eye image of the same patient.

Steps S320-S340 or S520-S540 are respectively performed on the left eye image and the right eye image to obtain a combined feature set of the left eye image and a combined feature set of the right eye image, then the combined feature set of the left eye image and the combined feature set of the right eye image are connected to generate a combined feature sequence, and the combined feature sequence is input into the classifier to obtain the classification result.

The classifier in this embodiment is obtained by training a combined feature set of both eyes which is served as the feature vector of the fundus image and obtained after processing by the first neural network and the second neural network. That is, the training for the classifier in this embodiment requires the input of the feature vector of the binocular length (which is twice the length of the monocular feature vector), and when predicting, it is also required to input the feature vector of the corresponding length to perform prediction.

The combined feature sequence in this embodiment includes the lesion features of the two different attributes of the left eye fundus image and the lesion features of the two different attributes of the right eye fundus image, which merges the binocular image (the lesions of both eyes have strong correlation), and also merges multiple CNN networks and quadrant lesion features, therefore further improving the accuracy of the lesion classification.

In one embodiment, the collected fundus image is two sets of fundus image pairs in different view fields, including a first view field left eye image, a first view field right eye image, a second view field left eye image and a second view field right eye image.

Steps S320-S340 or S520-S540 are respectively performed on the aforementioned binocular dual-view image to obtain four sets of combined feature sets. These combined feature sets are connected to generate a combined feature sequence. The combined feature sequence is input into the classifier to obtain the classification result.

The classifier in this embodiment is obtained by training a binocular dual-view combined feature set which is regarded as the feature vector of the fundus image and obtained after processing via the first neural network and the second neural network. In other words, the training for the classifier in this embodiment requires the input of the binocular dual-view length feature vector (which is 4 times the length of the monocular feature vector), and when predicting, it is also required to input the feature vector of the corresponding length to perform prediction.

If there is monocular or single-view data in the training data or the data to be predicted, the feature value corresponding to the unavailable/non-existing view field is set to be the same value of the existing view field, and the feature value corresponding to the unavailable/non-existing eye is set to be the same value of a certain existing single eye to generate a feature vector of the corresponding length.

The combined feature sequence in this embodiment includes two different attributes of the left eye fundus image in different view fields and two different attributes of the right eye fundus image in different view fields, which merges the dual-view binocular image and also merges multiple CNN networks and quadrant lesion features, therefore further improving the accuracy of lesion classification.

In one embodiment, a computer apparatus is provided, each module of which described below can be implemented in whole or in part by software, hardware, or a combination thereof in the computer apparatus. The computer apparatus includes following modules.

An image capturing module 710 is used to receive the collected fundus image.

A first neural network identification module 720 is used to identify the fundus image via a first neural network to generate a first feature set of the fundus image.

A second neural network identification module 730 is used to identify the fundus image via a second neural network to generate a second feature set of the fundus image, and the first feature set and the second feature set indicate different lesion attributes of the fundus image.

A feature combining module 740 is used to combine the first feature set and the second feature set to obtain a combined feature set of the fundus image.

A classification module 750 is used to input the combined feature set into the classifier to obtain a classification result.

In one embodiment, the first neural network is a convolutional neural network capable of identifying the types of the lesion included in a fundus image, the second neural network is a convolutional neural network capable of identifying the fundus lesion level, and the classifier is composed of a plurality of class II classification models in accordance with a preset classification logic.

In one embodiment, the first neural network identification module 720 is further used to quadrant-divide the fundus image to generate a quadrant image group; input each quadrant image of the quadrant image group into the first neural network to obtain a feature vector of each image; and combine the feature vectors of each quadrant image to generate the first feature set of the fundus image.

In one embodiment, the received fundus image includes a left eye fundus image and a right eye fundus image of the same patient. The classification module 750 is further used to connect the combined feature set of the left eye fundus image and the combined feature set of the right eye fundus image to generate a combined feature sequence of the fundus image; and input the combined feature sequence into the classifier to obtain the classification result.

In one embodiment, the received fundus image includes a first view field left eye fundus image, a second view field left eye fundus image, a first view field right eye fundus image, and a second view field right eye fundus image of the same patient. The classification module 750 is further used to connect a combined feature set of the first view field left eye fundus image, a combined feature set of the second view field left eye fundus image, a combined feature set of the first view field right eye fundus image, and a combined feature set of the second view field right eye fundus image to generate the combined feature sequence of the fundus image. The combined feature sequence is input into the classifier to obtain the classification result.

In one embodiment, the second neural network is a convolutional neural network capable of identifying the fundus lesion level. When the fundus image lesion includes n levels of the lesion, the generated second feature set is a feature vector with a length of n−1, and in the feature vector of the i-th level lesion, the i-th element and the elements prior to the i-th element are 1, and the rest elements are 0.

The specific definitions of the various modules of the computer apparatus refer to the above definition of the fundus image processing method, and details are not described herein again. Each module of the aforementioned computer apparatus can be implemented in whole or in part by software, hardware, and combinations thereof. The network interface can be an Ethernet card or a wireless network card, or the like. Each aforementioned module can be embedded in or independent of the processor of the computer apparatus in a hardware form, or can be stored in a memory of the computer apparatus in a software form, so that the processor invokes and executes the operations corresponding to the aforementioned modules. The processor can be a central processing unit (CPU), a microprocessor, a microcontroller, or the like.

Figure 8:
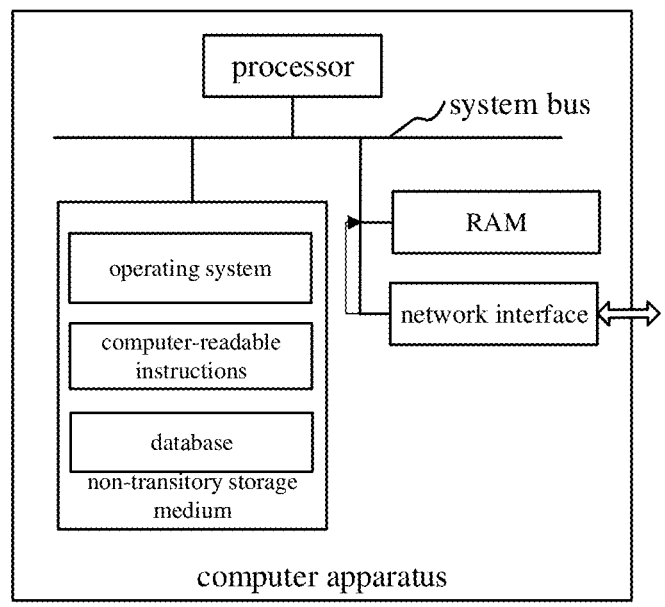
FIG. 8 is a block diagram of an internal structure of the computer apparatus in accordance with one or more embodiments.

In one embodiment, a computer apparatus is provided, which can be a server or a terminal, and whose block diagram can be as shown in FIG. 8. The computer apparatus includes a processor, a memory, a network interface, and a database which are connected via a system bus. The processor of the computer apparatus is used to provide computing and control capabilities. The memory of the computer apparatus includes a non-transitory storage medium, and a RAM. The non-transitory storage medium stores an operating system, computer-readable instructions, and the database. The RAM provides an environment for operation of the operating system and the computer-readable instructions in the non-transitory storage medium. The database of the computer apparatus is used to store neural network model data. The network interface of the computer apparatus is used to communicate with an external image capturing terminal via a network connection. The computer-readable instructions are executed by the processor to implement the fundus image processing method.

It will be understood by those skilled in the art that the structure shown in FIG. 8 is only a block diagram of a part of the structure related to the solution of the present application, and does not constitute a limitation of the computer apparatus to which the solution of the present application is applied. The specific computer apparatus can include more or fewer components than those shown in the figure, combine some components, or have different component arrangements.

A computer apparatus includes one or more processors and a memory storing computer-readable instructions, which, when executed by the one or more processors cause the one or more processors perform the steps of: receiving a collected fundus image; identifying the fundus image via a first neural network to generate a first feature set of the fundus image; identifying the fundus image via a second neural network to generate a second feature set of the fundus image, wherein the first feature set and the second feature set indicate different lesion attributes of the fundus image; combining the first feature set and the second feature set to obtain a combined feature set of the fundus image; and inputting the combined feature set into a classifier to obtain a classification result.

In one embodiment, the first neural network is a convolutional neural network capable of identifying a lesion type included in a fundus image, and the second neural network is a convolutional neural network capable of identifying a fundus lesion level, and the classifier is a multi-level classification network composed of a plurality of class II classifiers according to a preset classification logic.

In one embodiment, when the one or more processors perform the identifying the fundus image via the first neural network to generate the first feature set of the fundus image, the one or more processors further perform the steps of: quadrant-dividing the fundus image to generate a quadrant image group; inputting each quadrant image of the quadrant image group into the first neural network to obtain a feature vector of each quadrant image; and combining the feature vectors of each quadrant image to generate the first feature set of the fundus image.

In one embodiment, the collected fundus image includes a left eye fundus image and a right eye fundus image of the same patient; and when the one or more processors perform the inputting the combined feature set into the classifier to obtain the classification result, the one or more processors further perform the steps of: connecting a combined feature set of the left eye fundus image with a combined feature set of the right eye fundus image to generate a combined feature sequence of the fundus image; and inputting the combined feature sequence into the classifier to obtain the classification result.

In one embodiment, the collected fundus image includes a first view field left eye fundus image, a second view field left eye fundus image, a first view field right eye fundus image, and a second view field right eye fundus image of the same patient; and when the one or more processors perform the inputting the combined feature set into the classifier to obtain the classification result, the one or more processors further perform following steps: connecting a combined feature set of the first view field left eye fundus image, a combined feature set of the second view field left eye fundus image, a combined feature set of the first view field right eye fundus image, with a combined feature set of the second view field right eye fundus image to generate the combined feature sequence of the fundus image; and inputting the combined feature sequence into the classifier to obtain the classification result.

In one embodiment, the second neural network is a convolutional neural network capable of identifying a fundus lesion level, and when the fundus image lesion includes n levels of the lesion, the generated second feature set is a feature vector with a length of n−1, and in the feature vector of the i-th level lesion, the i-th element and the elements prior to the i-th element are 1 and the rest elements is 0.

One or more non-transitory storage medium store computer-readable instructions, which, when executed by one or more processors, cause the one or more processors to perform the steps of: receiving a collected fundus image; identifying the fundus image via a first neural network to generate a first feature set of the fundus image; identifying the fundus image via a second neural network to generate a second feature set of the fundus image, wherein the first feature set and the second feature set indicate different lesion attributes of the fundus image; combining the first feature set and the second feature set to obtain a combined feature set of the fundus image; and inputting the combined feature set into a classifier to obtain a classification result.

In one embodiment, the first neural network is a convolutional neural network capable of identifying a lesion type included in the fundus image, the second neural network is a convolutional neural network capable of identifying a fundus lesion level, and the classifier is multi-level classification network composed of a plurality of class II classifiers according to a preset classification logic.

In one embodiment, when the one or more processors perform the identifying the fundus image via the first neural network to generate the first feature set of the fundus image, the one or more processors further perform the steps of: quadrant-dividing the fundus image to generate a quadrant image group; inputting each quadrant image of the quadrant image group into the first neural network to obtain a feature vector of each quadrant image; and combining the feature vectors of each quadrant image to generate the first feature set of the fundus image.

In one embodiment, the collected fundus image includes a left eye fundus image and a right eye fundus image of the same patient; and when the one or more processors perform the inputting the combined feature set into the classifier to obtain the classification result, the one or more processors further perform the steps of: connecting a combined feature set of the left eye fundus image with a combined feature set of the right eye fundus image to generate a combined feature sequence of the fundus image; and inputting the combined feature sequence into the classifier to obtain the classification result.

In one embodiment, the collected fundus image includes a first view field left eye fundus image, a second view field left eye fundus image, a first view field right eye fundus image, and a second view field right eye fundus image of the same patient; and when the one or more processors perform the inputting the combined feature set into the classifier to obtain the classification result, the one or more processors further perform following steps: connecting a combined feature set of the first view field left eye fundus image, a combined feature set of the second view field left eye fundus image, a combined feature set of the first view field right eye fundus image, with a combined feature set of the second view field right eye fundus image to generate the combined feature sequence of the fundus image; and inputting the combined feature sequence into the classifier to obtain the classification result.

In one embodiment, the second neural network is a convolutional neural network capable of identifying a fundus lesion level, and when the fundus image lesion includes n levels of the lesion, the generated second feature set is a feature vector with a length of n−1, and in the feature vector of the i-th level lesion, the i-th element and the elements prior to the i-th element are 1 and the rest elements is 0.

A person skilled in the art should understand that the processes of the methods in the above embodiments can be, in full or in part, implemented by computer-readable instructions instructing underlying hardware. The computer-readable instructions can be stored in a computer-readable storage medium and the computer-readable instructions can include the processes in the embodiments of the various methods when it is being executed. Any references to memory, storage, databases, or other media used in various embodiments provided herein may include non-transitory and/or transitory memory. Non-transitory memory can include read only memory (ROM), programmable ROM (PROM), electrically programmable ROM (EPROM), electrically erasable programmable ROM (EEPROM), or flash memory. Transitory memory may include random access memory (RAM) or external high-speed cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), synchronization chain Synchlink DRAM (SLDRAM), memory Bus (Rambus) direct RAM (RDRAM), direct memory bus dynamic RAM (DRDRAM), memory bus dynamic RAM (RDRAM), and the like.

The technical features of the above embodiments can be arbitrarily combined. For the sake of brevity of description, all possible combinations of the technical features in the above embodiments are not described. However, as long as there is no collision in the combination of these technical features, it should be considered as the scope described in this specification.

The foregoing implementations are merely specific embodiments of the present disclosure, and are not intended to limit the protection scope of the present disclosure. It should be noted that any variation or replacement readily figured out by persons skilled in the art within the technical scope disclosed in the present disclosure shall all fall into the protection scope of the present disclosure. Therefore, the protection scope of the present disclosure shall be subject to the protection scope of the claims.

What is claimed is:

1. A method of processing fundus image, the method comprising:
   receiving a collected fundus image;
   identifying the collected fundus image via a first neural network to generate a first feature set of the collected fundus image, wherein the first feature set indicates a lesion type attribute of the collected fundus image, the second feature set indicates a lesion level attribute of the collected fundus image;
   identifying the collected fundus image via a second neural network to generate a second feature set of the collected fundus image, wherein the first feature set and the second feature set indicate different lesion attributes of the collected fundus image;
   combining the first feature set with the second feature set to obtain a combined feature set of the collected fundus image; and
   inputting the combined feature set into a classifier to obtain a classification result, wherein the inputting includes inputting the combined feature set containing the lesion type attribute and the lesion level attribute into a multi-level classifier composed of a plurality of class II classifiers according to a preset classification logic to obtain a multi-level classification result of the collected fundus image.

2. The method according to claim 1, wherein the identifying the collected fundus image via the first neural network to obtain the first feature set of the fundus image comprises:
   quadrant-dividing the fundus image to generate a quadrant image group;
   inputting each quadrant image of the quadrant image group into the first neural network to obtain a feature vector of each quadrant image; and
   combining the feature vectors of each quadrant image to generate the first feature set of the fundus image.

3. The method according to claim 1, wherein the received collected fundus image comprises a left eye fundus image and a right eye fundus image of the same patient;
   wherein the inputting the combined feature set into the classifier to obtain the classification result comprises:
      connecting a combined feature set of the left eye fundus image with a combined feature set of the right eye fundus image to generate a combined feature sequence of the collected fundus image; and
      inputting the combined feature sequence into the classifier to obtain the classification result.

4. The method according to claim 1, wherein the received collected fundus image comprises a first view field left eye fundus image, a second view field left eye fundus image, a first view field right eye fundus image, and a second view field right eye fundus image of the same patient;
   wherein the inputting the combined feature set into the classifier to obtain the classification result comprises:
      connecting a combined feature set of the first view field left eye fundus image, a combined feature set of the second view field left eye fundus image, a combined feature set of the first view field right eye fundus image, with a combined feature set of the second view field right eye fundus image to generate the combined feature sequence of the collected fundus image; and
      inputting the combined feature sequence into the classifier to obtain the classification result.

5. The method according to claim 1, wherein the identifying the collected fundus image via the second neural network to generate the second feature set of the collected fundus image comprises:
   identifying a lesion level attribute of the collected fundus image via the second neural network, and outputting a lesion level vector of the fundus image, wherein, when a fundus lesion is set to comprise n levels of the lesion, the generated lesion level vector has a length of n−1, wherein, in the feature vector of an i-th level lesion, the i-th element and the elements prior to the i-th element are configured as 1 and the rest elements are configured as 0.

6. The method according to claim 1, wherein after receiving the collected fundus image, the method further comprises:
   cropping the collected fundus image according to an information area of the collected fundus image; and
   preprocessing the cropped fundus image.

7. A computer apparatus comprising one or more processors and a memory storing computer-readable instructions, which, when executed by the one or more processors, causing the one or more processors to perform a method comprising:
   receiving a collected fundus image;

identifying the collected fundus image via a first neural network to generate a first feature set of the fundus image, wherein the first feature set indicates a lesion type attribute of the collected fundus image, the second feature set indicates a lesion level attribute of the collected fundus image;

identifying the collected fundus image via a second neural network to generate a second feature set of the collected fundus image, wherein the first feature set and the second feature set indicate different lesion attributes of the collected fundus image;

combining the first feature set and the second feature set to obtain a combined feature set of the fundus image; and inputting the combined feature set into a classifier to obtain a classification result, wherein the inputting includes inputting the combined feature set containing the lesion type attribute and the lesion level attribute into a multi-level classifier composed of a plurality class II classifiers according to a preset classification logic to obtain a multi-level classification result of the collected fundus image.

8. The computer apparatus according to claim 7, wherein when executing the computer-readable instructions, the one or more processors further perform the following steps:
quadrant-dividing the collected fundus image to generate a quadrant image group;
inputting each quadrant image of the quadrant image group into the first neural network to obtain a feature vector of each quadrant image; and
combining the feature vectors of each quadrant image to generate the first feature set of the collected fundus image.

9. The computer apparatus according to claim 7, wherein the received fundus image comprises a left eye fundus image and a right eye fundus image of the same patient; when executing the computer-readable instructions, the one or more processors further performs the following steps:
connecting a combined feature set of the left eye fundus image with a combined feature set of the right eye fundus image to generate a combined feature sequence of the collected fundus image; and
inputting the combined feature sequence into the classifier to obtain the classification result.

10. The computer apparatus according to claim 7, wherein the received fundus image comprises a first view field left eye fundus image, a second view field left eye fundus image, a first view field right eye fundus image, and a second view field right eye fundus image of the same patient; when executing the computer-readable instructions, the one or more processors further perform the following steps:
connecting a combined feature set of the first view field left eye fundus image, a combined feature set of the second view field left eye fundus image, a combined feature set of the first view field right eye fundus image, with a combined feature set of the second view field right eye fundus image to generate the combined feature sequence of the collected fundus image; and
inputting the combined feature sequence into the classifier to obtain the classification result.

11. The computer apparatus according to claim 7, wherein when executing the computer-readable instructions, the one or more processors further performs the following steps:
identifying a lesion level attribute of the collected fundus image via the second neural network, and outputting a lesion level vector of the fundus image, wherein, when a fundus lesion is set to comprise n levels of the lesion, the generated lesion level vector has a length of n−1, wherein, in the feature vector of an i-th level lesion, the i-th element and the elements prior to the i-th element are 1 and the numerals on the rest element are 0.

12. The computer apparatus according to claim 7, wherein after performing the receiving the collected fundus image, the one or more processors further perform the following steps:
cropping the collected fundus image according to an information area of the collected fundus image; and
preprocessing the cropped fundus image.

13. At least one non-transitory computer-readable storage medium storing computer-readable instructions, which, when executed by one or more processors, causing the one or more processors to perform a method comprising:
receiving a collected fundus image;
identifying the fundus image via a first neural network to generate a first feature set of the collected fundus image, wherein the first feature set indicates a lesion type attribute of the collected fundus image, the second feature set indicates a lesion level attribute of the collected fundus image;
identifying the fundus image via a second neural network to generate a second feature set of the collected fundus image, wherein the first feature set and the second feature set indicate different lesion attributes of the collected fundus image;
combining the first feature set and the second feature set to obtain a combined feature set of the collected fundus image; and
inputting the combined feature set into a classifier to obtain a classification result, wherein the inputting includes inputting the combined feature set containing the lesion type attribute and the lesion level attribute into a multi-level classifier composed of a plurality class II classifiers according to a preset classification logic to obtain a multi-level classification result of the fundus image.

14. The storage medium of claim 13, wherein the computer-readable instructions when executed by the one or more processors, further cause the one or more processors to perform the following steps:
quadrant-dividing the collected fundus image to generate a quadrant image group;
inputting each quadrant image of the quadrant image group into the first neural network to obtain a feature vector of each quadrant image; and
combining the feature vectors of each quadrant image to generate the first feature set of the collected fundus image.

15. The storage medium according to claim 13, wherein the received fundus image comprises a left eye fundus image and a right eye fundus image of the same patient; the computer-readable instructions when executed by the one or more processors, further cause the one or more processors to perform the following steps:
connecting a combined feature set of the left eye fundus image with a combined feature set of the right eye fundus image to generate a combined feature sequence of the collected fundus image; and
inputting the combined feature sequence into the classifier to obtain the classification result.

16. The storage medium according to claim 13, wherein the received fundus image comprises a first view field left eye fundus image, a second view field left eye fundus image, a first view field right eye fundus image, and a second view field right eye fundus image of the same patient; the computer-readable instructions when executed by the one or more processors, further cause the one or more processors to perform the following steps:
  connecting a combined feature set of the first view field left eye fundus image, a combined feature set of the second view field left eye fundus image, a combined feature set of the first view field right eye fundus image, with a combined feature set of the second view field right eye fundus image to generate the combined feature sequence of the collected fundus image; and
  inputting the combined feature sequence into the classifier to obtain the classification result.

17. The storage medium of claim 13, wherein the computer-readable instructions when executed by the one or more processors, further cause the one or more processors to perform the following steps:
  identifying a lesion level attribute of the fundus image via the second neural network and
  outputting a lesion level vector of the fundus image, wherein when a fundus lesion is set to comprise n levels of the lesion, the generated lesion level vector has a length of n−1, wherein, in the feature vector of an i-th level lesion, the i-th element and the elements prior to the i-th element are 1 and the rest elements are 0.

\* \* \* \* \*